United States Patent
Aven et al.

(10) Patent No.: US 6,894,003 B2
(45) Date of Patent: May 17, 2005

(54) ENHANCEMENT OF THE ACTIVITY OF CAROTENOID BIOSYNTHESIS INHIBITOR HERBICIDES

(75) Inventors: Michael Aven, Mainz (DE); Astrid Brandt, Mainz (DE); Norbert Nelgen, Jugenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/865,023

(22) Filed: May 24, 2001

(65) Prior Publication Data

US 2002/0039968 A1 Apr. 4, 2002

Related U.S. Application Data

(60) Provisional application No. 60/213,819, filed on Jun. 23, 2000, and provisional application No. 60/222,535, filed on Aug. 2, 2000.

(51) Int. Cl.$^7$ .................. A01N 25/08; A01N 25/10; A01N 23/40; A01N 43/54; A01N 43/56
(52) U.S. Cl. .................. 504/128; 504/130; 504/136; 504/242; 504/243; 504/250; 504/251; 504/252; 504/253; 504/256; 504/257; 504/358
(58) Field of Search .................. 504/128, 130, 504/136, 242, 243, 250, 251, 253, 256, 257, 252, 358

(56) References Cited

U.S. PATENT DOCUMENTS

| | | | |
|---|---|---|---|
| 4,875,925 A | * 10/1989 | Hewett et al. | 71/94 |
| 5,824,624 A |   10/1998 | Kleeman et al. | 504/242 |
| 5,849,758 A | * 12/1998 | Kleemann et al. | 514/269 |
| 5,851,952 A | * 12/1998 | Karp et al. | 504/251 |
| 6,030,924 A | *  2/2000 | Mayer et al. | 504/116 |
| 6,037,311 A |    3/2000 | Gosset et al. | 504/138 |
| 6,448,204 B1| *  9/2002 | Maier et al. | 504/250 |

FOREIGN PATENT DOCUMENTS

| | | |
|---|---|---|
| EP | 0 292 154 | 11/1988 |
| EP | 0 968 649 | * 1/2000 |

OTHER PUBLICATIONS

Konno et al. *"Synergistic herbicide compositions containing a nicotinamide derivative and a pyrazole derivative, for rice"* Chemical Abstracts vol. 109: 165724 (Abstract of JP 63/079804, published 1988), marked "XP–002191595".

Nilsson et al. *"Persistence and mobility of herbicides in arable soil. Investigations in 1986–1987"* Chemical Abstracts vol. 111: 128934 (Abstract of Swed. Crop Prot. Conf. (1989), 30$^{th}$(2), 270–277), marked "XP–002191600".

* cited by examiner

Primary Examiner—S. Mark Clardy
(74) Attorney, Agent, or Firm—Keil & Weinkauf

(57) ABSTRACT

The present invention provides a method for increasing the efficacy of a herbicidal compound of formula I

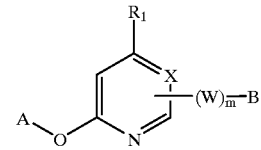

I which comprises applying an effective amount of said herbicidal compound directly to the soil in the form of a solid granule or solid powder which contains said herbicidal compound and at least one inert solid carrier.

It is another object of this invention to provide solid granular or powder compositions of herbicidal compounds of formula I and at least one inert solid carrier, as well as methods for the use of said compositions in the control of weeds.

11 Claims, No Drawings

ENHANCEMENT OF THE ACTIVITY OF CAROTENOID BIOSYNTHESIS INHIBITOR HERBICIDES

This application claims the benefit under 35 U.S.C. 119(e) of provisional applications 60/213,819 filed Jun. 23, 2000 and 60/222,535 filed Aug. 2, 2000.

BACKGROUND OF THE INVENTION

As a general rule, inert carrier ingredients must be used to formulate crop protection agents such as herbicidal compounds so that farmers can apply them conveniently and safely. The choice of formulation type and inert carrier ingredients often determines to a significant extent whether the active ingredient can express its full efficacy on application.

Farmers frequently apply pre-emergence herbicides and soil insecticides by broadcasting granular formulations directly onto the soil, as described, for example in "Chemistry and Technology of Agrochemical Formulations", edited by D. A. Knowles, Kluwer Academic Publishers, Dordrecht/Boston/London, 1998 (ISBN 0-7514-0442-8) p. 71. Granular formulations of soil-applied herbicides can provide considerable advantages under practical field conditions because planting and application can be carried out in a single operation, thus saving time and money. This application method, while convenient, does not necessarily ensure that the activity of the crop protection agent will be fully expressed.

The International Patent Application WO 92/22204 suggests that for certain benzamide herbicides such as isoxaben (N-[3-(1-ethyl-1-methylpropyl)-5-isoxazolyl]-2,6-dimethyxybenzamide), the mobility in the soil and/or the herbicidal efficacy can be increased by applying these compounds in the presence of cyclodextrins.

Certain carotenoid biosynthesis inhibitor herbicides are described in GB 2,087,887, EP 0 447 004 B1, WO 94/22833, EP 0 692 474 B1, EP 0 693 490 B1, EP 0 694 538 A2, EP 0 723 960 A1, WO 98/56789 and EP 0 902 026 A1. The efficacy of said herbicides when applied to the soil can sometimes be diminished due to their tendency to bind to the soil. Said binding reduces bioavailability and prevents the full expression of herbicidal activity.

It is an object of this invention to provide methods for enhancing the pre-emergence performance of said herbicidal agents. It is another object of this invention to provide solid granular or powder compositions of carotenoid biosynthesis inhibitor herbicides and at least one inert solid carrier, as well methods for the use of said compositions in the control of weeds.

SUMMARY OF THE INVENTION

In accordance with the objects of this invention, it has now been found that the pre-emergence herbicidal performance of compounds of structural formula I

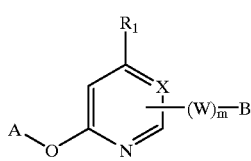

wherein

A and B each independently represent a phenyl, pyridyl, pyrazolyl or thienyl ring being optionally substituted by one or more halogen atoms, alkyl, haloalkyl or haloalkoxy groups;

$R_1$ represents a hydrogen or halogen atom or an alkyl or alkoxy group;

X represents CH or N;

W represents —O—, —OCH2— or —CONH—, and m is 0 or 1 is increased by applying an effective amount of said herbicidal compound directly to the soil in which the plants are cultivated in the form of a solid granule or powder which contains said herbicidal compound and at least one inert solid carrier.

Furthermore, the invention relates to a method for the control of undesired weeds at a locus which comprises treating said locus with a solid granule according to the invention.

These and other objects and features of the invention will become more apparent from the detailed description set forth hereinbelow.

DETAILED DESCRIPTION OF THE INVENTION

Although carotenoid biosynthesis inhibitor herbicides such as those described in GB 2,087,887, EP 0 447 004 B1, WO 94/22833, EP 0 692 474 B1, EP 0 693 490 B1, EP 0 694 538 A2, EP 0 723 960 A1, WO 98/56789 and EP 0 902 026 A1 are effective herbicidal agents, there is ongoing research to provide means for maximizing the expression of herbicidal activity under field conditions so that the rate of said required for effective weed control can be kept to a minimum, both for economic and environmental reasons.

Surprisingly, it has now been found that the pre-emergence herbicidal performance of compounds of structural formula I

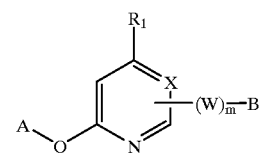

wherein A, B, X, W, $R_1$ and m are defined as above is improved by applying an effective amount of said herbicidal compound directly to the soil in which the plants are cultivated in the form of a solid granule or powder which contains said herbicidal compound and at least one inert solid carrier.

Preferred herbicidal compounds I are those regioisomers of structural formula IA

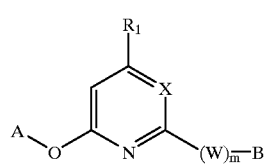

wherein

A represents a group of formula a, b, c or d:

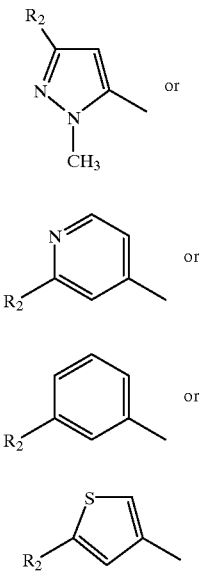

wherein $R_2$ is a halogen atom or a $C_{1-3}$haloalkyl or $C_{1-3}$haloalkoxy group, most preferred a chlorine atom, or a trifluoromethyl, pentafluoroethyl, trifluoromethoxy or difluoromethoxy group.

More preferred are those compounds of formula IA wherein

A and B each independently represent a phenyl being optionally substituted by one or more halogen atoms, alkyl, haloalkyl or haloalkoxy groups;

$R_1$ represents a hydrogen or halogen atom or an alkyl or alkoxy group;

X represents CH or N; and

W represents —CONH—, and m is 0 or 1.

Most preferred are 2',4'-difluro-2-(α,α, α-trifluoro-m-tolyloxy)nicotinamide (diflufenican), N-(4-fluorophenyl)-6-[3-trifluoromethyl)phenoxy]-2-pyridine carboxamide (picolinafen) or 4-(3-trifluoromethylphenoxy)-2-(4-trifluoromethylphenyl)-pyrimidine, hereinafter referred to as TTP.

The term "optionally substituted" as used hereinbefore and hereinbelow refers to a group or moiety which may be unsubstituted or substituted by one or more, preferably one or two, substituents.

The terms "alkyl, alkoxy, haloalkyl or haloalkoxy" as used hereinbefore and hereinbelow refers to an alkyl, haloalkyl or haloalkoxy group or moiety with up to 12, preferably 1 to 6, in particular 1 to 4 carbon atoms. The haloalkyl and haloalkoxy groups refer to alkyl or alkoxy groups which are substituted by one or more halogen atoms, preferably fluorine atoms. Preferred are the fluoroalkyl and fluoroalkoxy groups of formula

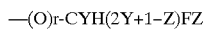

—(O)r-CYH(2Y+1-Z)FZ wherein r represents 0 or 1, Y represents an integer from 1 to 12, and Z represents an integer from 1 to an integer of 2Y+1. Most preferred alkyl, haloalkyl or haloalkoxy groups are methyl, ethyl, propyl, butyl, methoxy, ethoxy, trifluoromethyl, 2,2,2-trifluoroethyl, pentafluoroethyl and trifluoromethoxy.

The term "halogen" as used hereinbefore and hereinbelow refers to a fluorine, chlorine, bromine or iodine atom, preferably a fluorine or chlorine atom, more preferably a fluorine atom.

It is also an object of this invention to provide solid granular or powder compositions of herbicidal compounds of structural formula I

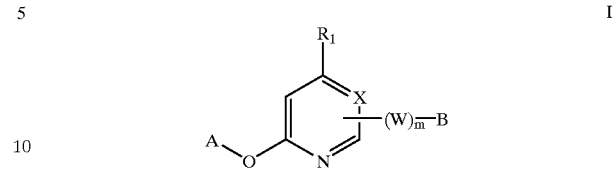

wherein A, B, X, W, $R_1$ and m are defined as above and at least one inert solid carrier.

Most surprisingly, the granules and powders used according to the present invention also expand the efficacy profile of the compounds of formula I since these compositions can be successfully applied in normal application amounts to control weeds on crop on which they had previously required uneconomically high doses of the compounds of formula I. Another advantage of the unique pre-emergence application technique of the invention is that the herbicide can be applied during seed planting. A separate trip to the field to apply the herbicide is then not necessary.

The solid granules comprise the following:

(a) About 0.1 to about 100 g/kg of at least one herbicidal compound of formula I; and (b) About 900 to about 999.9 g/kg of one or more inert solid carriers and optimally, one or more solid auxiliaries.

Conventionally used solid carriers may be used in the solid granules and powders according to the present invention. Preferably used are such solid materials, which are essentially insoluble in water and have large surfaces and/or high absorbencies, in particular, natural mineral powders such as kaolin, argillaceous earth, talcum, chalk, quartz, atapulgite, montmorillonite and synthetic mineral powders such as silicic acid, alumina and silicates. The solid carriers are preferably selected from the group consisting of granular gypsum, clays such as kaolin or bentonite, silica, inorganic salts, polyvinylpyrrolidone, polyvinylacetate, cyclodextrin, sugar and mixtures or co-polymers thereof, such as, for example, cross linked polyvinylpyrrolidone, polyvinylacetate vinylpyrrolidone, etc. and optionally at least one solid auxiliary. A particularly preferred solid carrier is cyclodextrin.

Conventionally used additional solid ingredients may be used in the solid granules according to the present invention. Preferably disintegrants, which are highly soluble in water, in particular, salts such as potassium sulfate, ammonium sulfate, potassium carbonate, sodium hydrogen carbonate (sodium bicarbonate) and sodium acetate trihydrate are utilized.

The solid formulation according to the present invention preferably comprises 0 to about 10% by weight, in particular, 0 to about 5% by weight of at least one disintegrant.

Further solid ingredients are dispersants or wetting agents. Suitable dispersants are so-called water-soluble soaps, as well as water-soluble synthetic surface-active compounds. Soaps usually are alkali, earth alkali or optionally substituted ammonium salts of higher fatty acids ($C_{10}$–$C_{20}$), e.g. the sodium or potassium salts of oleic or stearic acid or of mixtures of natural fatty acids which are prepared, for example, from coconut or tallow oil. Furthermore, methyl-taurine salts of fatty acids may be used. However, so-called synthetic surfactants are preferably used, especially fatty sulfonates, fatty sulfates or alkyl aryl sulfonates. The fatty sulfates or fatty sulfonates are normally used as alkali, earth alkali or optionally substituted ammonium salts and have an alkyl moiety of 8 to 22 carbon atoms, whereby alkyl also means the alkyl moiety of acyl residues, such as the sodium or calcium salt of lignin sulfonic acid, of sulfuric acid dodecylate, or of a mixture of fatty alcohols prepared from natural fatty acids, in particular, sodium lignin sulfonate. This also includes the salts of sulfuric acid esters, sulfonic acids and adducts of fatty alcohols and ethylene oxide. Alkyl aryl sulfonates are, for example, the sodium, calcium or triethyl ammonium salts of dodecyl benzene sulfonic acid, dibutyl naphthalene sulfonic acid or of a condensate of naphthalene sulfonic acid and formaldehyde. Furthermore, phosphates, such as the salts of the phosphoric acid ester of a p-nonylphenol(4–14)-ethylene oxide adduct or phospholipids, may be used. In addition, non-ionic dispersants may be used. Preferred are block polymers obtainable from propylene oxide and ethylene oxide, in particular, block polymers which consist of a polyoxypropylene core having a molecular weight of about 3,000 to about 3,500 and the remainder having a combined molecular weight of about 6,000 to 7,000 comprising ethylene oxide units.

In preferred embodiments, the dispersants are selected from the commercially available components:

Tensiofix LX special, a sodium lignin sulfonate available from Omnichem S. A., 1348 Louvain-La-Neuve, Belgium;

Ufoxane 3 A, a sodium lignin sufonate, (available from Borregaard);

Borresperse NH, an ammonium lignin sufonate, (available from Borregaard);

Geropon TA/72, a sodium polycarboxylate (available from Rhodia);

Soprophor AS/222, an ethoxylated fatty alcohol adsorbed on silica, (available from Rhodia); and Pluronic PE 10500, a block polymer obtained from propylene oxide and ethylene oxide, (available from BASF Corporation).

The solid formulation according to the present invention preferably comprises 0 to about 25% by weight, in particular 0 to about 15% of at least one dispersant.

Suitable wetting agents are, as a rule, salts of long chained alkyl sulfates. The fatty sulfates are normally used as alkali, earth alkali or optionally substituted ammonium salts and have an alkyl moiety of 8 to 22 carbon atoms. Particularly preferred is sodium lauryl sulfate, commercially obtainable as Tensiofix BCZ, a sodium alkyl sulfate, available from Omnichem S.A., or as Rewopol NLS 90 available from Witco GmbH, Germany.

The solid formulation according to the present invention preferably comprises 0 to about 10% by weight, in particular, 0 to about 2.5% of at least one wetting agent.

The solid carrier preferably comprises at least one cyclodextrin of formula II

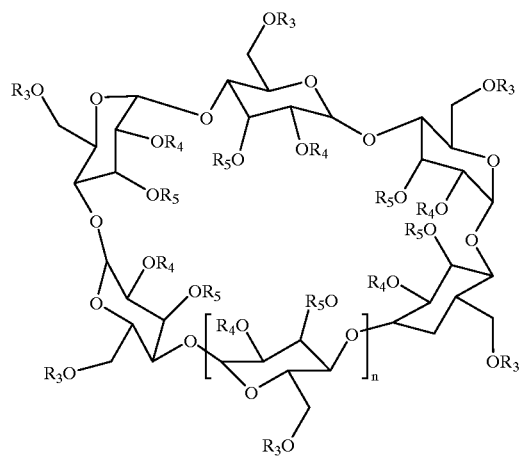

wherein
$R_3$, $R_4$ and $R_5$ each independently represent a hydrogen atom or a $C_{1-4}$alkyl, $C_{1-4}$alkanoyl or a $C_{1-4}$hydroxy alkyl group; and
n is 1, 2 or 3.

The cyclodextrins, wherein $R_3$ through $R_5$ represent a hydrogen group are particularly preferred. Most preferred is β-cyclodextrin (n=2).

In another preferred embodiment of the present invention the solid carrier comprises the following:
(b1) About 50 to about 250 g/kg of one or more cyclodextrin of formula II, in particular β-cyclodextrin; and
(b2) About 650 to about 949.9 g/kg of one or more solid carrier selected from the group consisting of granular gypsum, clays such as kaolin or bentonite, silica, inorganic salts, polyvinylpyrrolidone, polyvinylacetate, sugar and mixtures or co-polymers thereof and optionally, at least one solid auxiliary.

The herbicidal compositions of this invention may comprise other compounds having biological activity in addition to the herbicides of formula I, e.g. compounds having similar or complementary herbicidal activity or compounds having plant growth regulating, fungicidal or insecticidal activity.

These mixtures of herbicides can have a broader spectrum of activity than the compound of general formula I alone.

Examples of the other herbicidal compounds are acifluorfen, aclonifen, alachlor, alloxydim, ametryn, amitrole, anilazine, anilofos, asulam, atrazine, azinphosmethyl, benazolin, benfluralin, benfuresate, bensulide, bentazone, benzofenap, bifenox, bromacil, brombutide, bromoxynil, butachlor, butamifos, butenachlor, butylate, carfentrazone-ethyl, chloramben, chlorbromuron, chlorbufam, chlorimuron, chlornitrofen, chlorotoluron, chlorthiamid, cinmethylin, clomozone, clopyralid, cyanazine, cycloate, 2,4-D, daimuron, desmetryn, dicamba, dichlobenil, dichloroprop-P, diclofop-methyl, diflufenican, dimefuron, dimepiperate, dimethachlor, dimethatryn, dimehtenamid, dinitramine, dinoterb, dithiopyr, esprocarb, ethafluralin, ethofumesate, ethoxyfen-ethyl, fenoxaprop, fenuron, flamprop-M-isopropyl, flamprop-M-methyl, fluazifop, fluchloralin, flufenacet, flumioxazin, fluometuron, fluoroglycofen, flupoxam, fluridone, flurochloridone, flurprimidol, flurtamone, fluthiacet-methyl, fomesafen, glufosinate, haloxyfop, ioxynil, isoxaflutole, lactofen, linuron, mecoprop, mecoprop-P, mefenacet, metazachlor, metobenzuron, metobromuron, metolachlor, metoxuron, monolinuron, naproanilide, napropamide, naptalam, norflurazon, orbencarb, oxadiazon, oxyfluorfen, pebulate, pendimethalin, picloram, pretilachlor, prodiamine, prometon, prometryn, propachlor, propanil, propisochlor, propyzamide, prosulfocarb, pyrazoxyfen, pyributicarb, siduron, tebuthiuron, terbacil, terbumeton, terbuthylazine, terbutryn, thiazopyr, thiobencarb, tiocarbazil, triallate, triclopyr and trifluralin.

The appropriate relative amounts of active ingredient of formula I and the total amount of solid carrier is in accordance with the invention, between approximately 1:500 and 1:2, preferably between approximately 1:200 and 1:5 and, in particular, between approximately 1:125 and 1:10.

It is also an object of this invention to provide methods for the use of the solid granular or powder formulations of the invention in the control of weeds.

The compositions according to the invention possess a high herbicidal activity within a wide concentration range and at low dosages, and may readily be used in agriculture, especially for the selective control of undesired plants such as *Alopecurus myosuroides, Echinochloa crus-galli, Lolium perenne, Setaria viridis, Galium aparine, Matricaria inodora vulgare, Papaver rhoeas, Stellaria media, Veronica persica, Lamium purpureum, Viola arvensis, Abutilon theophrasti, Ipomoea purpurea* and *Amaranthus retroflexus* by pre-emergence application, and particularly in certain crops, such as cereals, in particular barley and wheat, maize and rice.

Recommended doses for various applications in the absence of a solid carrier are known for the herbicidal compounds of formula I. The efficacy thereof can be enhanced in accordance with the invention. For instance, addition of the carriers disclosed herein can surprisingly and beneficially reduce the amount of active ingredient per hectare required in these recommendations by half or more (depending on the active ingredient, the carrier and their respective amounts), so that additional weeds can be controlled at reasonable doses of the compound of formula I.

Surfactants may be nonionic, anionic, cationic or zwitterionic substances with good dispersing, emulsifying and wetting properties depending on the nature of the compound according to general formula I to be formulated. Surfactants may also include mixtures of individual surfactants.

Examples of formulations according to the invention are shown in the following formulations A through G. Ingredients used in these formulations are shown below.

Ingredients Used in Formulations A–G

| Trade Name | Chemical Identity |
| --- | --- |
| Agrimer ® XL | Polyvinylpyrrolidone (PVP) |
| Agrimer ® VA-6 | Crosslinked Copolymer of vinyl pyrrolidone and vinyl acetate |
| Alpha W6 | α-cyclodextrin |
| Beta W7 | β-cyclodextrin |
| Gamma W8 | γ-cyclodextrin |
| Tensiofix ® BCZ | sodium alkyl sulfate |
| Tensiofix ® LX Special | lignosulfonate |

Formulation A: TTP 1 g/kg GR Kaolin Granules

| Ingredient | Component | Amount [g/kg] |
| --- | --- | --- |
| TTP | active ingredient | 1.0 |
| Tensiofix ® LX Special | Dispersant | 90.0 |
| Tensiofix ® BCZ | wetting agent | 10.0 |
| Agrimer XL | disintegrant | 20.0 |
| kaolin | carrier | 879.0 |

The ingredients are milled together. Subsequently, 15 wt. percent of water is added and the resulting pasty mass is granulated. The resulting granules are dried in a fluidized bed dryer at 40° C. for 15 minutes.

Formulations B to D: TTP Cyclodextrin Powder and Granules

| | | Amount (g) | | |
| --- | --- | --- | --- | --- |
| Ingredient | Component | B | C | D |
| TTP | active ingredient | 1.5 | 0.2 | 2.0 |
| Alpha W6 | Carrier | 4.4 | — | — |
| Beta W7 | Carrier | — | 0.6 | — |
| Gamma W8 | Carrier | — | — | 6.0 |
| Water | Auxiliary | 23.2 | 26.0 | 23.2 |

The active ingredient is milled to a particle diameter of <15μm using a pin mill. The cyclodextrin is dissolved in water at 30 to 40° C. Subsequently, the milled active ingredient is added and the mixture is heated to 65° C. The mixture is then vigorously mixed for 15 minutes. Finally the water is evaporated to yield the cyclodextrin complex as a white powder which is dried for 3 days at 30° C.

Formulation E: TTP 10 g/kg Cyclodextrin/Sugar Granules or Powder

| Ingredient | Component | Amount (g) |
| --- | --- | --- |
| Formulation D | active ingredient-cyclodextrin complex | 0.4 |
| Sugar | Carrier | 8.8 |

The ingredients are milled together to yield a homogenous powder. The mixture is then compressed into small granules. The ungranulated powder can be applied as such or mixed with other materials to be applied directly to the soil such as a fertilizer.

Formulation F: TTP 50 g/kg GR Polyvinylpyrrolidone Granules

| Ingredient | Component | Amount (g) |
| --- | --- | --- |
| TTP | active ingredient | 50.0 |
| Agrimer VA-6 | carrier | 950.0 |

The ingredients are dissolved in 500 ml of isopropanol in a round-bottomed flask under heating to 40° C. The solvent is evaporated in vacuo using a rotary evaporator. The resulting flakes are removed from the flask using a spatula.

Formulation G: TTP 10 g/kg GR Cyclodextrin/ Granular Gypsum

| Ingredient | Component | Amount (g) |
|---|---|---|
| Formulation D | active ingredient-cyclodextrin complex | 2.5 |
| Granular gypsum | Carrier | 25.0 |

The ingredients are mixed together in a shaker bottle and shaken for 2 minutes at ambient temperature to yield granules coated with Formulation D.

To illustrate the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

EXAMPLE 1

Greenhouse Comparison of the Pre-emergence Herbicidal Efficacy of Granular Formulations of TTP with Unformulated Technical TTP Seeds of the monocotyledonous and dicotyledonous test plants are separately mixed with potting soil and planted on top of approximately one inch of soil in separate pint cups. After planting, the cups are subjected to the following treatments:

| TREATMENT | INGREDIENTS |
|---|---|
| H | TTP technical (dispersion in acetone) |
| I | TTP 1 g/kg GR GR (kaolin + Agrimer XL) |
| J | TTP 10 g/kg GR GR (PVP: Agrimer VA 6) |
| K | TTP 10 g/kg Powder GR (cyclodextrin: gamma WS) |

Technical TTP (treatment H) is applied as a dispersion in acetone using a single-nozzle overhead track pneumatic sprayer, while granular or powder formulations (treatments I–K) are applied by shaking the solid granules or powder directly and evenly onto the soil surface.

The treated cups are then placed on greenhouse benches, watered and cared for in accordance with conventional greenhouse procedures. Twenty days after treatment (DAT), the seedling plants are examined, and the % weed control as compared to untreated check is recorded (Table I). Crop phytotoxicity is assessed visually at 11 and 20 DAT and is given in Table II.

As can be seen from Tables I and II, a clear increase in activity of TTP results from the granular formulations of TTP in comparison with unformulated TTP. This increase is most pronounced (4×) with the cyclodextrin granules K, which control *Alopecurus* and *Galium* at 60 g/ha while 240 g/ha are required with the unformulated technical TTP dispersion in acetone.

TABLE I

| | | Weed Control (20 DAT) | | | | | | |
|---|---|---|---|---|---|---|---|---|
| TREATMENT | Rate [kg/ha] | ALOMY | LOLPE | SETVI | GALAP | MATIN | PAPRH | VERPE |
| H | 0.480 | 99.0 | 99.0 | 100.0 | 98.0 | 100.0 | 100.0 | 100.0 |
| TTP Technical | 0.240 | 98.5 | 99.0 | 100.0 | 98.0 | 99.0 | 100.0 | 100.0 |
| (Acetone | 0.120 | 77.5 | 98.5 | 100.0 | 72.5 | 99.0 | 99.5 | 100.0 |
| Solution) | 0.060 | 22.5 | 91.5 | 96.5 | 67.5 | 98.5 | 99.5 | 99.5 |
| I | 0.480 | 100.0 | 99.0 | 100.0 | 100.0 | 100.0 | 100.0 | 100.0 |
| Granule | 0.240 | 99.0 | 99.0 | 100.0 | 100.0 | 100.0 | 100.0 | 100.0 |
| TTP (1 g/kg) | 0.120 | 75.0 | 99.0 | 100.0 | 100.0 | 99.0 | 100.0 | 99.0 |
| Kaolin & Agrimer XL | 0.060 | 70.0 | 98.0 | 100.0 | 100.0 | 99.0 | 98.0 | 99.0 |
| | 0.030 | 25.0 | 80.0 | 100.0 | 80.0 | 98.0 | 99.0 | 99.0 |
| J | 0.480 | 100.0 | 99.0 | 100.0 | 100.0 | 99.0 | 100.0 | 100.0 |
| Granule | 0.240 | 98.0 | 98.0 | 100.0 | 100.0 | 100.0 | 100.0 | 100.0 |
| TTP (10 g/kg) | 0.120 | 85.0 | 80.0 | 100.0 | 100.0 | 99.0 | 100.0 | 100.0 |
| PVP: Agrimer VA 6 | 0.060 | 95.0 | 100.0 | 100.0 | 100.0 | 99.0 | 99.0 | 100.0 |
| K | 0.480 | 100.0 | 99.0 | 100.0 | 100.0 | 100.0 | 100.0 | 100.0 |
| Powder | 0.240 | 100.0 | 99.0 | 100.0 | 100.0 | 100.0 | 100.0 | 100.0 |
| TTP (10 g/kg) | 0.120 | 99.0 | 99.0 | 100.0 | 100.0 | 100.0 | 100.0 | 99.0 |
| Cyclodextrin gamma WS | 0.0600 | 90.0 | 99.0 | 100.0 | 90.0 | 98.0 | 100.0 | 99.0 |
| Untreated | — | 0.0 | 0.0 | 0.0 | 0.0 | 0.0 | 0.0 | 0.0 |

TABLE II

| | | Crop Phytotoxicity | | | |
|---|---|---|---|---|---|
| | Rate | 11 DAT | | 20 DAT | |
| Treatment | [kg/ha] | HORVWM | TRZAWK | HORVWM | TRZAWK |
| H | 0.480 | 47.5 | 14.0 | 45.0 | 10.0 |
| TTP Technical | 0.240 | 42.5 | 6.5 | 40.0 | 4.5 |
| (Acetone | 0.120 | 40.0 | 2.5 | 25.0 | 1.0 |
| Solution) | 0.060 | 20.0 | 1.0 | 15.0 | 0.5 |
| I | 0.480 | 55.0 | 35.0 | 50.0 | 18.0 |
| Granule | 0.240 | 50.0 | 25.0 | 50.0 | 15.0 |
| TTP (1 g/kg) | 0.120 | 40.0 | 3.0 | 40.0 | 2.0 |
| Kaolin & Agrimer XL | 0.060 | 40.0 | 2.0 | 40.0 | 2.0 |
| J | 0.480 | 50.0 | 35.0 | 70.0 | 22.0 |
| Granule | 0.240 | 45.0 | 22.0 | 45.0 | 15.0 |
| TTP (10 g/kg) | 0.120 | 45.0 | 18.0 | 45.0 | 15.0 |
| PVP: Agrimer VA 6 | 0.060 | 40.0 | 5.0 | 35.0 | 1.0 |
| K | 0.480 | 93.0 | 75.0 | 99.0 | 75.0 |
| Granule | 0.240 | 75.0 | 65.0 | 70.0 | 55.0 |
| TTP (10 g/kg) | 0.120 | 60.0 | 30.0 | 60.0 | 18.0 |
| Cyclodextrin gamma WS | 0.060 | 40.0 | 12.0 | 35.0 | 5.0 |
| Untreated | — | 0.0 | 0.0 | 0.0 | 0.0 |

Plant Species Employed in Herbicidal Evaluations

| Header Abbr. | Common Name | Scientific Name |
|---|---|---|
| TRZAWK | Wheat, Winter (variety Kanzler) | *Triticum aestivum* (variety Kanzler) |
| HORVWM | Barley, Winter (variety Mammut) | *Hordeum vulgare* (variety Mammut) |
| ALOMY | Blackgrass | *Alopecurus myosuroides* |
| LOLPE | Ryegrass | *Lolium perenne* |
| SETVI | Green foxtail | *Setaria viridis* |
| GALAP | Galium | *Galium aparine* |
| MATIN | Matricaria | *Matricaria inodora vulgare* |
| PAPRH | Poppy | *Papaver rhoeas* |
| VERPE | Veronica | *Veronica persica* |

What is claimed is:

1. A solid granule which comprises about (a) 0.1 to 100 g/kg of at least one herbicidal compound of formula IA

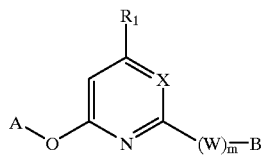

IA wherein
A represents a group of formula a, b, c, or d:

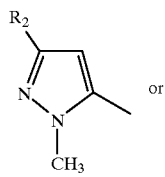

(a)

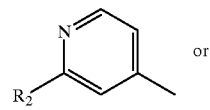

(b)

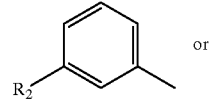

(c)

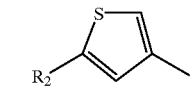

(d)

wherein $R_2$ is a halogen atom or a $C_{1-3}$ haloalkyl or $C_{1-3}$ haloalkoxy group;

B represents a phenyl, pyridyl, pyrazolyl or thienyl ring being optionally substituted by one or more halogen atoms, alkyl, aloalkyl or haloalkoxy groups;

$R_1$ represent a hydrogen or halogen atom or an alkyl or alkoxy group;

X represents CH or N;

W represents —O—, —OCH$_2$— or —CONH—, and m is 0 or 1; and (b) 900 to 999.9 g/kg of one or more solid carrier comprising a cyclodextrin of formula II

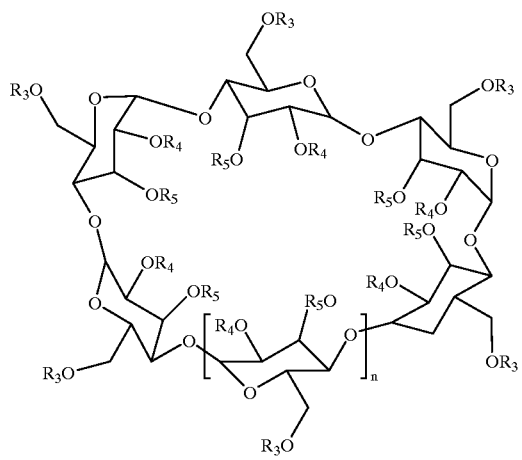

wherein
R₃, R₄ and R₅ each independently represent a hydrogen atom or a $C_{1-4}$ alkyl, $C_{1-4}$ alkanoyl or a $C_{1-4}$ hydroxyalkyl group; and
n is 1, 2 or 3.

2. A solid granule according to claim 1, wherein the solid carrier is a cyclodextrin of formula II, wherein R₃, R₄ and R₅ each represent a hydrogen atom and n is 2.

3. A solid granule according to claim 1, which comprises (b1) 50 to 250 g/kg of one or more cyclodextrin of formula II; and (b2) 650 to 949.9 g/kg of one or more solid carrier selected from the group consisting of
granular gypsum, kaolin or bentonite, silica, inorganic salts, polyvinylpyrrolidone, polyvinylacetate, sugar and mixtures or copolymers thereof and optionally at least one solid auxiliary.

4. A method for the control of undesired weeds at a locus which comprises treating said locus with an effective amount of the solid granule defined in claim 1.

5. A method according to claim 4 wherein said weeds are *Galium* spp. or *Alopecurus* spp.

6. The method according to claim 4, wherein R² is a chlorine atom, or a trifluoromethyl, pentafluoroethyl, trifluoromethoxy or difluoromethoxy group.

7. A solid granule which consists essentially of (a) 0.1 to 100 g/kg of at least one herbicidal compound which is 2',4'-difluoro-2-(α,α,α-triflouro-m-tolyloxy)-nicotinamide (diflufenican); and (b) 900 to 999.9 g/kg of one or more solid carrier comprising a cyclodextrin of formula II

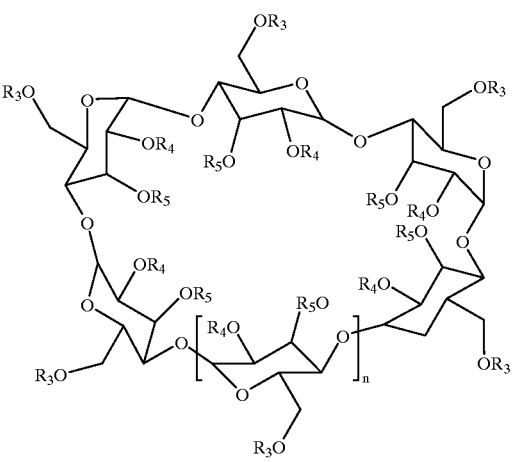

wherein
R₃, R₄ and R₅ each independently represent a hydrogen atom or a $C_{1-4}$ alkyl, $C_{1-4}$ alkanoyl or a $C_{1-4}$ hydroxyalkyl group; and
n is 1, 2 or 3;
and optionally at least one solid auxiliary.

8. The solid granule according to claim 7, wherein R₃, R₄ and R₅ each represent a hydrogen atom and n is 2.

9. The solid granule according to claim 7, which comprises (b1) 50 to 250 g/kg of one or more cyclodextrin of formula II; and (b2) 650 to 949.9 g/kg of one or more solid carrier selected from the group consisting of
granular gypsum, kaolin or bentonite, silica, inorganic salts, polyvinylpyrrolidone, polyvinylacetate, sugar and mixtures or copolymers thereof, and optionally at least one solid auxiliary.

10. A method for the control of undesired weeds at a locus which comprises treating said locus with a solid granule which consists essentially of (a) 0.1 to 100 g/kg of at least one herbicidal compound which is 2',4'-difluoro-2(α,α,α-trifluoro-m-tolyloxy)-nicotinamide (diflufenican); and (b) 900 to 999.9 g/kg of one or more solid carrier comprising a cyclodextrin of formula II

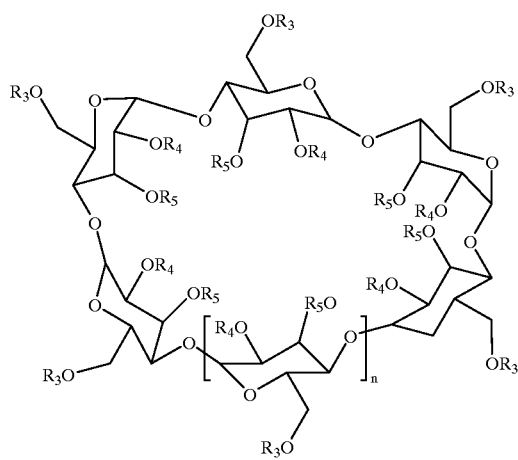
II
wherein
R$_3$, R$_4$ and R$_5$ each independently represent a hydrogen atom or a C$_{1-4}$ alkyl, C$_{1-4}$ alkanoyl or a C$_{1-4}$ hydroxyalkyl group; and
n is 1, 2 or 3;
and optionally at least one solid auxiliary.
11. The method according to claim 10 wherein said weeds are *Galium* spp. or *Alopecurus* spp.
* * * * *